US009267113B2

(12) United States Patent
Wu et al.

(10) Patent No.: US 9,267,113 B2
(45) Date of Patent: Feb. 23, 2016

(54) HYBRID BACULOVIRUS AND USES THEREOF

(71) Applicant: Chung Yuan Christian University, Jhongli, Taoyuan County (TW)

(72) Inventors: Tzong-Yuan Wu, Panchiao (TW); Mean-Shine Chen, Jhongli (TW); Chao-Yi Teng, Jhongli (TW); Ying-Ju Chen, Shinyuan Township, Ping Tung County (TW); Chung-Hsiung Wang, Tainan (TW)

(73) Assignee: CHUNG YUAN CHRISTIAN UNIVERSITY, Jhongli, Taoyuan County (TW)

( * ) Notice: Subject to any disclaimer, the term of this patent is extended or adjusted under 35 U.S.C. 154(b) by 43 days.

(21) Appl. No.: 14/203,489

(22) Filed: Mar. 10, 2014

(65) Prior Publication Data

US 2015/0252332 A1 Sep. 10, 2015

(51) Int. Cl.
*C12N 7/00* (2006.01)
*A01K 67/02* (2006.01)
*A01K 67/027* (2006.01)

(52) U.S. Cl.
CPC .............. *C12N 7/00* (2013.01); *A01K 67/0271* (2013.01); *A01K 2227/706* (2013.01); *A01K 2267/01* (2013.01); *C12N 2710/14041* (2013.01)

(58) Field of Classification Search
None
See application file for complete search history.

(56) References Cited

PUBLICATIONS

Betting et al., "Enhanced immune stimulation by a therapeutic lymphoma tumor antigen vaccine produced in insect cells involves mannose receptor targeting to antigen presenting cells". 2009 Vaccine 27 (2): 250-9.
Zerbino DR et al. in "Velvet: algorithms for de novo short read assembly using de Bruijn graphs" (Genome research 2008, 18 (5): 821-829).
Chen YR et al. in "Genomic and host range studies of Maruca vitrata nucleopolyhedrovirus" (J. General Virology 2008, 89: 2315-2330).

*Primary Examiner* — Addison D Ault
(74) *Attorney, Agent, or Firm* — Muncy, Geissler, Olds & Lowe, P.C.

(57) ABSTRACT

Disclosed herein is an *Autographa californica* multiple nucleopolyhedrovirus (AcMNPV) based hybrid baculovirus and its uses thereof. The AcMNPV based hybrid baculovirus is capable of infecting different hosts, and comprises *Maruca vitrata* multiple nucleopolyhedrovirus (MaviMNPV) genes of lef1, orf1629, pk1, CDS1, CDS2, and lef2; and AcMNPV/MaviMNPV-hybrid genes of egt and orf152. The AcMNPV based hybrid baculovirus is therefore useful as a bio-insecticide by its capability of delivering genes of toxic proteins to be expressed in at least two different insect hosts.

15 Claims, 5 Drawing Sheets

FIG 1

(A) Sf21 cells

Mock | vAc-egfp | Hybrid-AcMv | egfp-Mavi

(B) NTU-MV532 cells

Mock | vAc-egfp | Hybrid-AcMv | egfp-Mavi

(A) Sf21 cells (B) High-Five cells

FIG 3

(C) NTU-MV532 cells

FIG 4

SEQUENCE LISTING

```
<160> NUMBER OF SEQ ID NOS: 3

<210> SEQ ID NO 1
<211> LENGTH: 1524
<212> TYPE: DNA
<213> ORGANISM: AcMNPV/MaviMNPV-hybrid virus
<220> FEATURE:
<221> NAME/KEY: egt gene
<222> LOCATION: (1)..(1524)

<400> SEQUENCE: 1
atgattgttc ttcactgctg gcttgtactg ttgtgtacat ttaatactgt aaacacggct     60
aatatattag ccgtgtttcc tatgccagct tacagccacc acatagtata cagagtgtat    120
atcgaagctc tggctgaaca atgtcacaac gttacggtca ttaagcccaa attgtttgcg    180
tattcaaaca aaacttattg tggcaatatc acggaaatcg atgccgacat gtccgtcgag    240
tactacaaga aattggtgtc aaattcggca atgtttagaa aacgcggcgt ggtgtccgac    300
acaaacactg tgaccgccgc taattacgtg cacttgattg aaatgttcaa agaccagttt    360
```

```
gataatatca aagtgcgcaa ttttattacc aacaaccaaa cattcgactt ggttgtggtg    420
gaagcgtttg ccgactatgc gctggtgttt ggtcacttgt acgatccggc gcctgtaatc    480
caaatcgcgc ctggttatgg tttggcggag aactttgaca cgatcggagc cgtggcgcga    540
catcccatcc atcatcctaa catttggcgt gacaattttg acgccacaga ggagaacacg    600
atgacggaaa ttcgattgta taaagaattc aaaattttaa ccaacttgtc caactcgttg    660
ctcaaacaac agtttggacc gaatactccg acaattgaag aattacgcaa taaagtacag    720
ctgctcttgc taaacctgca tcccatattt gacaacaacc gacccgtgcc tcccagcgtg    780
caatatctcg gaggaggcat tcatcttagg ccggcccaaa taacgcgttg attacttcga    840
ccatcagcac tcgtataaac aaatcaaaga gaaaatagt  ctacgtaagt tttggatcga    900
gcattgatac caaatcgttt gctaacgagt tcttgacat  gttaattgac acgttcaaaa    960
gattgaaaaa cttaactata ttattgaaag attgatgacg aggtagtgaa aaatgtcacg   1020
ttgcccgcca acgtaatcac tcaaagttgg ttcaatcaac gcgccgtgtt aaatcacggg   1080
aaaacggccg tatttattac gcaaggcggt ttacaatcga gcgacgaggc cttagaagcc   1140
cgggtgccca tggtgtgtct gcccatgatg ggtgaccagt tttatcacgc acaccagtta   1200
cagaaactcg gcgtggcccg cgccttggac actgttacag tttccagcga tcaactgcta   1260
atggcgataa cgacgtgtt  gtttaacgcg cctacctaca aaaaacacat ggccgagtta   1320
tatgcgctca tcaatcatga taagcaacg  tttccgcctc tagataaagc catcaaattc   1380
acagaacgcg taattcgata tagacatgac atcagtcgtc aattgtattc attaaaaaca   1440
acagctgcca atgtaccgta ttcaaattac tacatgtata aatctgtgtt ttctattgta   1500
atgaatcact aacacactt  ttaa                                          1524

<210> SEQ ID NO 2
<211> LENGTH: 280
<212> TYPE: DNA
<213> ORGANISM: AcMNPV/MaviMNPV-hybrid virus
<220> FEATURE:
<221> NAME/KEY: orf152 gene
<222> LOCATION: (1)..(280)

<400> SEQUENCE: 2
atgaattttt ttgtaatgca aaaaaagtca cgttcgccag caccccctata tacagtacaa     60 agtctacaaa tcgtagacta ttttattaga atagtctaca ctgtacgata cgctcccaat    120
atactactac actatcaact tttttgcatt acaaaaaagt tcatttttgc ctggcaagtt    180 tcccaacca  ctattgtctt atcagtcgtg cagtactgat aaacagtata aatacagctg    240
ccgttctact cgtaagcaca gttcaagcct cacagcctag                          280

<210> SEQ ID NO 3
<211> LENGTH: 110
<212> TYPE: DNA
<213> ORGANISM: Rhopalosiphum padi virus 5'-UTR
<220> FEATURE:
<221> NAME/KEY: promoter
<222> LOCATION: (1)..(110)

<400> SEQUENCE: 3
agttaaagct ttataactat aagtaagccg tgccgaaacg ttaatcggtc gctagttgcg     60
taacaactgt tagtttaatt ttccaaaatt tattttttcac aattttttagt              110
```

HYBRID BACULOVIRUS AND USES THEREOF

BACKGROUND OF THE INVENTION

1. Field of the Invention

The present disclosure relates to hybrid virus. Specifically, the present disclosure relates to novel *Autographa californica* multiple nucleopolyhedrovirus (AcMNPV) based hybrid baculovirus capable of infecting at least two different hosts.

2. Description of Related Art

The baculoviruses have been divided into four genera: *Alphabaculovirus* (nucleopolyhedroviruses (NPVs) isolated from *Lepidoptera*), *Betabaculoviruses* (granuloviruses (GV) isolated form *Lepidoptera*), *Gammabaculoviruses* (NPVs isolated from hymenoptera) and *Deltabaculoviruses* (NPVs isolated from Dipter). While GVs contain only one nucleocapsid per envelope, NPVs contain either single (SNPV) or multiple (MNPV) nucleocapsids per envelope. The enveloped virions are further occluded in granulin matrix in GVs and polyhedrin in NPVs.

Baculoviruses have a restricted range of hosts that they can infect, which is typically restricted to a limited number of closely related insect species. Since baculoviruses are not harmful to humans, they are considered to be a safe option as biological agents to produce exogenous proteins in baculoviruses—permissive insect cells or larvae. For example, proteins produced by baculoviruses have been used as therapeutic cancer vaccines with several immunologic advantages over proteins derived from mammalian sources (Betting et al., "Enhanced immune stimulation by a therapeutic lymphoma tumor antigen vaccine produced in insect cells involves mannose receptor targeting to antigen presenting cells". 2009 *Vaccine* 27 (2): 250-9).

What would be useful for the application of baculoviruses in industry or in agriculture, would be to devise improved baculoviruses with a wider host range that they can infect, hence allowing baculoviruses carrying genes of proteins of interest to be used in mass protein production method; or as bioinsecticides, for a wider range of insect hosts may be reached.

SUMMARY

The present disclosure provides a novel AcMNPV based hybrid baculovirus capable of infecting at least two different insect hosts and its uses for producing exogenous proteins such as toxic proteins in these hosts. Accordingly, the novel AcMNPV hybrid baculovirus is useful as a cross host bioinsecticide, for at least two different insect hosts are permissive to this novel AcMNPV hybrid baculovirus.

It is the first object of the present disclosure to provide an *Autographa californica* multiple nucleopolyhedrovirus (AcMNPV) based hybrid baculovirus capable of infecting at least two different hosts. The AcMNPV based hybrid baculovirus comprises at least *Maruca vitrata* multiple nucleopolyhedrovirus (MaviMNPV) genes of lef1, orf1629, pk1, CDS1, CDS2, and lef2; and AcMNPV/MaviMNPV-hybrid genes of egt (SEQ ID NO: 1) and orf152 (SEQ ID NO:2).

In some optional embodiments, the AcMNPV based hybrid baculovirus may further include a first nucleic acid encoding a first fluorescent protein, which is any of green fluorescence protein (GFP), enhanced green fluorescence protein (EGFP), *Discosoma* sp. red fluorescent protein (DsRed), blue fluorescence protein (BFP), enhanced yellow fluorescent proteins (EYFP), *Anemonia majano* fluorescent protein (amFP), *Zoanthus* fluorescent protein (zFP), *Discosoma* fluorescent protein (dsFP), or *Clavularia* fluorescent protein (cFP).

The AcMNPV based hybrid baculovirus is capable of infecting both AcMNPV-permissive cells or insect larvae, as well as MaviMNPV-permissive cells or insect larvae. According to some examples, the AcMNPV-permissive cells may be any of *S. furgiperda* IPBL-9 (Sf9), Sf21 or High-five (Hi-5) cells; and the AcMNPV-permissive insect larvae are *Trichoplusia ni* or *Spodoptera frugiperda*. In other examples, the MaviMNPV-permissive cells are NTU-MV532 cells; and the MaviMNPV-permissive insect larvae are *Maruca Vitrata*.

It is the second object of the present disclosure to provide a method of producing an exogenous protein in an insect host. The method includes steps of:

(a) co-transfecting the insect host with the AcMNPV based hybrid baculovirus having a first nucleic acid encoding the first fluorescent protein of the present disclosure, and a transfer vector, wherein the transfer vector comprises in sequence, a promoter, a second nucleic acid operably linked to the promoter and encodes the exogenous protein, an IRES element, and a third nucleic acid operably linked to the IRES element and encodes a second fluorescent protein, wherein the first and second fluorescent proteins emit fluorescence at different wavelengths;

(b) isolating the transfected host that emits fluorescence of the second fluorescent protein;

(c) cultivating the isolated host of step (b); and (d) harvesting the exogenous protein from the cultivated host of step (c).

According to one preferred embodiment of the present disclosure, the IRES element of the transfer vector is a portion of a *Rhopalosiphum padi* virus (RhPV) IRES sequence at least 90% identical to SEQ ID NO: 3.

According to preferred embodiments of the present disclosure, the insect host may be AcMNPV-permissive cells or insect larvae, as well as MaviMNPV-permissive cells or insect larvae. According to further examples, the AcMNPV-permissive cells may be any of Sf9, Sf21 or Hi-5 cells; and the AcMNPV-permissive insect larvae are *Trichoplusia ni* or *Spodoptera frugiperda*. In other examples, the MaviMNPV-permissive cells are NTU-MV532 cells; and the MaviMNPV-permissive insect larvae are *Maruca Vitrata*.

According to embodiments of the present disclosure, the exogenous protein may be any of an insect toxic protein, a therapeutic protein or a reporter protein. In one example, the exogenous protein is an insect toxic protein, preferably a protein toxic to *Lepidoptera*.

In some embodiments of the present disclosure, the first and second fluorescent proteins may be respectively selected from the group consisting of GFP, EGFP, DsRed, BFP, EYFP, amFP, zFP. dsFP, and cFP. In one preferred example, the first and second fluorescent proteins are EGFP and DsRed, respectively.

The details of one or more embodiments of the invention are set forth in the accompanying description below. Other features and advantages of the invention will be apparent from the detail descriptions, and from claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects and advantages of the present invention will become better understood with reference to the following description, appended claims and the accompanying drawings, where:

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. DEFINITION

"Nucleotide sequence", "polynucleotide" or "nucleic acid" can be used interchangeably and are understood to mean, according to the present disclosure, either a double-stranded DNA, a single-stranded DNA or products of transcription of the said DNAs (e.g., RNA molecules). It should also be understood that the present disclosure does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

The percentage of identity between a subject sequence and a reference standard can be determined by submitting both sequences to a computer analysis with any parameters affecting the outcome of the alignment set to the default position. Optimal alignment of sequences for aligning a comparison window are well known to those skilled in the art and may be conducted by tools such as the homology alignment algorithm, include, but are not limited to GAP, BESTFIT, FASTA, and TFASTA (Accelrys Inc., Burlington, Mass., USA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more nucleic acid sequences may be to a full-length nucleic acid sequence or a portion thereof, or to a longer nucleic acid sequence. In some instances, a subject sequence and the reference standard can exhibit the required percent identity without the introduction of gaps into one or both sequences. In many instances, the extent of identity will be evident without computer assistance The term "operably linked" refers to nucleotide sequences which are linked in the proper reading frame, whether to encode a mRNA transcript of a desired gene product or for a desired regulatory control. Operably linked can also mean that both the first and second nucleic acids are encoded by the same transcription unit. Translation of both such proteins can be regulated by various modes, including cap-dependent translation of the first open-reading-frame (ORF) located furthermost 5' on the transcription unit. Translation of the second ORF located downstream of the first ORF can be regulated by an IRES. Alternatively, both the first and second genes can be encoded by one ORF, yielding one contiguous polypeptide with both biological activities.

The term "toxic" as used herein meant that the exogenous proteins produced by the method of the present disclosure with the aid of the identified AcMNPV based hybrid baculovirus are lethal to *Lepidoptera* insects.

The singular forms "a", "and", and "the" are used herein to include plural referents unless the context clearly dictates otherwise.

II. DESCRIPTION OF THE INVENTION

The practices of this invention are hereinafter described in detail with respect to a novel AcMNPV based hybrid baculovirus capable of infecting at least two different insect hosts. This novel AcMNPV based hybrid baculovirus are thus useful as a means for producing exogenous proteins, such as insect toxic proteins, in at least two different insect hosts, hence the novel AcMNPV based hybrid baculovirus of the present disclosure may act as an insecticide capable of reaching a wider range of hosts.

The first objective of the present disclosure is to provide an *Autographa californica* multiple nucleopolyhedrovirus (AcMNPV) based hybrid baculovirus. The AcMNPV based hybrid baculovirus is capable of infecting at least two different hosts and is characterized in having at least *Maruca vitrata* multiple nucleopolyhedrovirus (MaviMNPV) genes of lef1, orf1629, pk1, CDS1, CDS2, and lef2; and AcMNPV/MaviMNPV-hybrid genes of egt (SEQ ID NO: 1) and orf152 (SEQ ID NO:2).

The AcMNPV based hybrid baculovirus of the present disclosure is produced by co-infecting a first insect host, such as an AcMNPV-permissive insect cell line or larvae or a MaviMNPV-permissive cell line or larvae, with a recombinant AcMNPV virus capable of expressing a first fluorescent protein, and a recombinant MaviMNPV virus capable of expressing a second fluorescent protein, in which the first and second fluorescent protein emit fluorescence at different wavelengths. In one preferred embodiment, the first host is an AcMNPV-permissive insect cell line Sf21.

Suitable fluorescent protein that may be used in the present disclosure includes, but is not limited to, green fluorescence protein (GFP), enhanced green fluorescence protein (EGFP), *Discosoma* sp. red fluorescent protein (DsRed), blue fluorescence protein (BFP), enhanced yellow fluorescent proteins (EYFP), *Anemonia majano* fluorescent protein (amFP), *Zoanthus* fluorescent protein (zFP), *Discosoma* fluorescent protein (dsFP), and *Clavularia* fluorescent protein (cFP). According to one preferred example, the recombinant AcMNPV virus and the recombinant MaviMNPV virus are engineered to express DsRed and EGFP, respectively. Accordingly, the first insect host of Sf21 cells successfully infected with the recombinant AcMNPV virus will emit red fluorescence due to the expression of DsRed, whereas those Sf21 cells successfully infected with the recombinant MaviMNPV virus will emit green fluorescence. If, however, the Sf21 cells were successfully co-infected with both recombinant viruses, then an emission of a yellow fluorescence is expected due to the expression of both DsRed and EGFP. Accordingly, Sf21 cells emitting yellow fluorescence are chosen and the supernatant of these cells are collected and used to infect another batch of insect cells; the cultivation is monitored by the expression of fluorescent proteins until a single plaque is obtained.

To verify whether the virus collected from the single plaque contains hybrid genes, a second insect host, or a host differs from the previous host of Sf21 cells is subsequently infected with such virus. In one preferred example, the second insect host is MaviMNPV-permissive cells or larvae. Amplification procedures are repeated again until another single viral plaque is obtained, and virus collected therefrom is subject to whole genome sequence analysis, which confirmed the identified hybrid virus is AcMNPV based hybrid baculovirus and comprises at least *Maruca vitrata* multiple nucleopolyhedrovirus (MaviMNPV) genes of lef1, orf1629, pk1, CDS1, CDS2, and lef2; and AcMNPV/MaviMNPV-hybrid genes of egt (SEQ ID NO: 1) and orf152 (SEQ ID NO:2).

According to the preferred embodiment of the present disclosure, the AcMNPV/MaviMNPV-hybrid gene of egt (SEQ ID NO: 1) is at least 85% identical to its AcMNPV counterpart or its MaviMNPV counterpart; whereas the AcMNPV/MaviMNPV-hybrid gene of orf152 (SEQ ID NO:2) is at least 90% identical to its AcMNPV counterpart and at least 60% identical to its MaviMNPV counterpart.

Further, the AcMNPV based hybrid baculovirus is characterized in containing the nucleic acid that encodes the second fluorescent protein originated from the recombinant MaviMNPV virus in its genomic DNA. Suitable fluorescent protein includes, but is not limited to, GFP, EGFP, DsRed, BFP, EYFP, amFP, zFP, dsFP, and cFP. In the preferred example, the AcMNPV based hybrid baculovirus is characterized in containing the nucleic acid that encodes EGFP.

The thus identified AcMNPV based hybrid baculovirus is capable of infecting both AcMNPV-permissive cells or insect larvae, as well as MaviMNPV-permissive cells or insect larvae. In some examples, the AcMNPV-permissive cells may be any of Sf9, Sf21 or Hi-5 cells; and the AcMNPV-permissive insect larvae are *Trichoplusia ni* or *Spodoptera frugiperda*. In other examples, the MaviMNPV-permissive cells are NTU-MV532 cells; and the MaviMNPV-permissive insect larvae are *Maruca Vitrata*.

Since the afore-identified AcMNPV based hybrid baculovirus is capable of infecting at least two different types of insect hosts, it is therefore a useful means for delivering foreign genes to different insect hosts. Accordingly, the second object of the present disclosure is to provide a method of producing an exogenous protein in an insect host by use of the AcMNPV based hybrid baculovirus of the present disclosure.

In the present method, an insect host, either AcMNPV-permissive or MaviMNPV-permissive cells or insect larvae are co-transfected with the afore-identified AcMNPV based hybrid baculovirus of the present disclosure, which contains a first nucleic acid encoding a first fluorescence protein (e.g., EGFP), and a transfer vector. The transfer vector is constructed to comprise in sequence, a promoter, a second nucleic acid operably linked to the promoter and encodes the exogenous protein, an internal initiation of translation (IRES) element, and a third nucleic acid operably linked to the IRES element and encodes a second fluorescent protein; in which the first and second fluorescent proteins emit fluorescence at different wavelengths. The extent of transfection of the insect host is monitored by the expression of the first and second fluorescent proteins respectively delivered by the AcMNPV based hybrid baculovirus of the present disclosure and the transfer vector. If homologous recombination occurred between the AcMNPV based hybrid baculovirus of the present disclosure and the transfer vector, the DNA segment comprising the first fluorescent protein in the AcMNPV based hybrid baculovirus of the present disclosure would be replaced by the DNA segment comprising the exogenous protein and the second fluorescent protein of the transfer vector, therefore, allowing the AcMNPV based hybrid baculovirus of the present disclosure to deliver and express the exogenous protein gene carried by the transfer vector, to and in the insect host, by monitoring the co-expressed second fluorescent protein (such as DsRed) in the host. The insect host that emits the second fluorescence protein may then be isolated and further amplified, so as to mass produce the exogenous protein.

Suitable promoter for use in the transfer vector is any of a polyhedrin (polh) promoter, a cytomegalovirus (CMV) promoter, a CAG promoter composed of chicken β-actin promoter and CMV enhancer, and etc. In one example, the promoter is a polh promoter.

IRES sequences are distinct regions of RNA molecules that are able to attract the eukaryotic ribosome to the mRNA molecule and, therefore, allow translation initiation to occur. It is common that IRESes are located at the 5'-untranslated region (5'UTR) of some RNA viruses such as small RNA viruses or hepatitis C viruses and allow translation of the RNAs in a cap-independent manner. When an IRES element is placed between two open reading frames (ORFs) in an eukaryotic mRNA molecule, it can drive translation of the downstream protein coding region independently of the 5'-cap structure bound to the 5'-end of the mRNA molecule. In such setup, both proteins are produced in the host cell. Any known IRES sequence, either natural or chimeric, may be used to construct the transfer vector of in the present disclosure. According to preferred embodiments of the present disclosure, the IRES element of the transfer vector is a portion of a *Rhopalosiphum padi* virus (RhPV) IRES sequence at least 90% identical to SEQ ID NO: 3.

Exogenous proteins that may be expressed in the insect host using the AcMNPV based hybrid baculovirus of the present disclosure include at least, therapeutic proteins, insect toxic proteins or a combination thereof. Accordingly, depending on the desired exogenous proteins to be expressed, the AcMNPV based hybrid baculovirus of the present disclosure may turn the insect host into a bio-factory for mass production of therapeutic proteins, which include, but are not limited to, albumin, globulins (e.g., α-globulin), monoclonal antibodies, interferons, insulin, epidermal growth factor (EGF), erythropoietin, blood factors, and blood clotting factors. Alternatively, the AcMNPV based hybrid baculovirus of the present disclosure may carry genes of insect toxic proteins, preferably, proteins that are toxic to *Lepidoptera*, and act as a bio-insecticide that is effective to at least two different insect hosts. Examples of insect toxic proteins include, but are not limited to, ricin, cholera toxin, botulism toxin, scorpion neurotoxin or diphtheria toxin.

According to preferred embodiments of the present disclosure, the insect host may be AcMNPV-permissive cells or insect larvae, as well as MaviMNPV-permissive cells or insect larvae. According to further examples, the AcMNPV-permissive cells may be any of Sf9, Sf21 or Hi-5 cells; and the AcMNPV-permissive insect larvae are *Trichoplusia ni* or *Spodoptera frugiperda*. In other examples, the MaviMNPV-permissive cells are NTU-MV532 cells; and the MaviMNPV-permissive insect larvae are *Maruca Vitrata*.

In some embodiments of the present disclosure, the first and second fluorescent proteins may be respectively selected from the group consisting of GFP, EGFP, DsRed, BFP, EYFP, amFP, zFP, dsFP, and cFP. In one preferred example, the first and second fluorescent proteins respectively conferred by the AcMNPV based hybrid baculovirus of the present disclosure and the transfer vector are EGFP and DsRed, respectively.

To provide those skilled in the art the tools to use the present disclosure, the AcMNPV based hybrid baculovirus and host cells of this invention may be assembled to kits. The components included in the kits are viral vector, enzymatic agents for making recombinant viral constructs, cells for amplification of the viruses, and reagents for transfection and transduction into the host cells, as well as description in a form of pamphlet, tape, CD, VCD or DVD on how to use the kits.

The following examples illustrate the construction and identification of the hybrid baculovirus of the present invention and the use thereof in the production of an exogenous protein in two different insect hosts. The examples are illustrative only, and do not limit the scope of the present invention.

EXAMPLES

Materials and Methods

Cell Culture

*S. furgiperda* IPBL-sf21 insect cell line (herein after "Sf21 cells") and NTU-MV532 cells derived from insect larvae of *Maruca Vitrata* were cultured in TNM-FH medium containing 8-10% heat-inactivated fetal bovine serum (FBS) until a confluent cell monolayer was obtained.

Measurement of EGFP or DsRed in Cell Extract

Four days after viral infection, the infected cells were lysed in 300 μl of lysing solution containing 100 mM potassium phosphate (pH 7.8), 1 mM EDTA, 10% Triton X-100, and 7 mM β-mercaptoethanol. After centrifugation at 15,200×g for 30 min, the lysate supernatant (100 μl) was taken for fluorescence measurement. The fluorescence intensities of EGFP and DsRed were measured using a Cary Eclipse Fluorescence spectrophotometer (Varian) with excitation and emission wavelength set at 488 nm and 507 nm, respectively.

Whole Genome Sequencing

The genome of the hybrid AcMv of example 1.2 was sequenced by Illumina MiSeq (Re-sequencing, 2×250 bp). The sequence was De novo assembly by Zerbino D R et al. in "Velvet: algorithms for de novo short read assembly using de Bruijn graphs" (Genome research 2008, 18 (5): 821-829).

Western Blot Analysis

After the cells were infected with the recombinant viruses for 4 days, the proteins in the cell extracts were separated by SDS-PAGE according to the procedure of Laemmli on a mini ProteinII system (Bio-Rad). The SDS-PAGE separated proteins were electrotransferred to a PVDF (polyvinyldiene difluoride) membrane (Millipore), which was then blocked with Tris-buffered saline (TTBS: 100 mM Tris, pH 7.4, 100 mM NaCl, and 0.1% Tween 20) containing 5% BSA (Sigma) at room temperature for 1 h with gentle shaking on an orbital shaker. Subsequently, membranes were incubated overnight at 4 with PBS-diluted (1:2000) anti-PCV2 antibody. Unbound antibodies were removed by three 5-min washes in TTBS buffer at room temperature with shaking. Membranes were then incubated with 1:2.500 diluted alkaline phosphate (AP) secondary antibodies (Jackson) for 1 h at room temperature. The AP on the membrane was detected by an enhanced chemiluminescence kit (Pierce) following the protocol provided by the manufacturer.

Example 1

Generation and Characterization of Hybrid AcMv Baculovirus 1.1 Plasmid Construction and Virus Generation 1.1.1 Construction and Generation of egfp-Mavi The egfp-Mavi was constructed in accordance with the procedures described by Chen Y R et al. in "Genomic and host range studies of *Maruca vitrata* nucleopolyhedrovirus" (J. General Virology 2008, 89: 2315-2330).

1.1.2 Construction and Generation of Ac-DsRed

The DsRed gene (derived from plasmid pDsRed-N1, ClonTech, USA) was subcloned into the pBlubac4.5 transfer vector and the resulting plasmid was named pBacDsRed. The pBacDsRed (0.8 ug) was cotransfected with viral DNA Bac-N-Blue (0.2 ug, Invitrogen, USA) into Sf21 cells using Cellfectin (1 ul, Invitrogen, USA) and the resulting recombinant virus was purified by end point dilution and named Ac-DsRed.

1.1.3 Construction and Generation of Ac-egfp

The egfp gene (derived from plasmid pEGFP-C1, ClonTech, USA) was subcloned into the pBlubac4.5 transfer vector and the resulting plasmid was named pBacDsRed. The pBacDsRed (0.8 ug) was cotransfected with viral DNA Bac-N-Blue (0.2 ug, Invitrogen, USA) into Sf21 cells using Cellfectin (1 ul, Invitrogen, USA) and the resulting recombinant virus was purified by end point dilution and named Ac-egfp.

1.1.4 Construction of pMv-L-PCV2-RP110-DsRed

The fragment of PCV2-RP110-DsRed was chemically synthesized and cloned into pUC18 cloning vector to generate the plasmid pUC18-PCV2-RP110-DsRed. The baculovirus transfer vector pMv-polh-total with XhoI was then digested and ligated with the PCV2-RP110-DsRed DNA fragment (derived from pUC18-PCV2-RP110-DsRed by restriction enzyme XhoI and Sal) by T4 DNA ligase and the resultant recombinant transfer plasmid was named pMv-L-PCV2-RP110-DsRed.

1.2 Generation of Hybrid AcMv Baculovirus

*Spodoptera frugiperda* 21 (Sf21) cells were seeded at a density of $2 \times 10^5$/well and cultivated in a media containing 10% FBS. Half an hour later, the cells were co-infected with egfp-Mavi virus of example 1.1.1 and recombinant Ac-DsRed virus of example 1.1.2 at the multiplicity of infection (moi) of 1 and 10, respectively. 1.5 to 2 hours after the infection, the media were replaced by fresh culture media supplemented with 10% FBS, and the cells were incubated at 27° C. for 5 days to allow the recombination of egfp-Mavi virsus and Ac-DsRed virus. As depicted in photographs in FIG. 1A, cells successfully infected with recombinant egfp-Mavi virus of example 1.1.1 emitted green fluorescence (view under FITC filter), whereas cells successfully infected with Ac-DsRed virus of example 1.1.2 emitted red fluorescence (view under rhodamine filter). It was noted that some cells exhibited yellow fluorescence, indicating the cells co-infected with the two viruses, in which both EGFP and DsRed were expressed that give rise to the merged yellow fluorescence. Such observation implied that the vAc-DsRed virus might help the expression of EGFP from the egfp-Mavi virus of example 1.1.1 in the MaviMNPV-non-permissive Sf21 cells. The culture medium of the co-infected cells that emitted yellow fluorescence was then collected and used to infect another batch of Sf21 cells. The photographs of a single plaque illustrated in FIG. 1B indicate that a cluster of cells, instead of sporadic cells, were co-infected with the two different kinds of viruses that emitted fluorescence at two different wavelengths.

Figure 1:
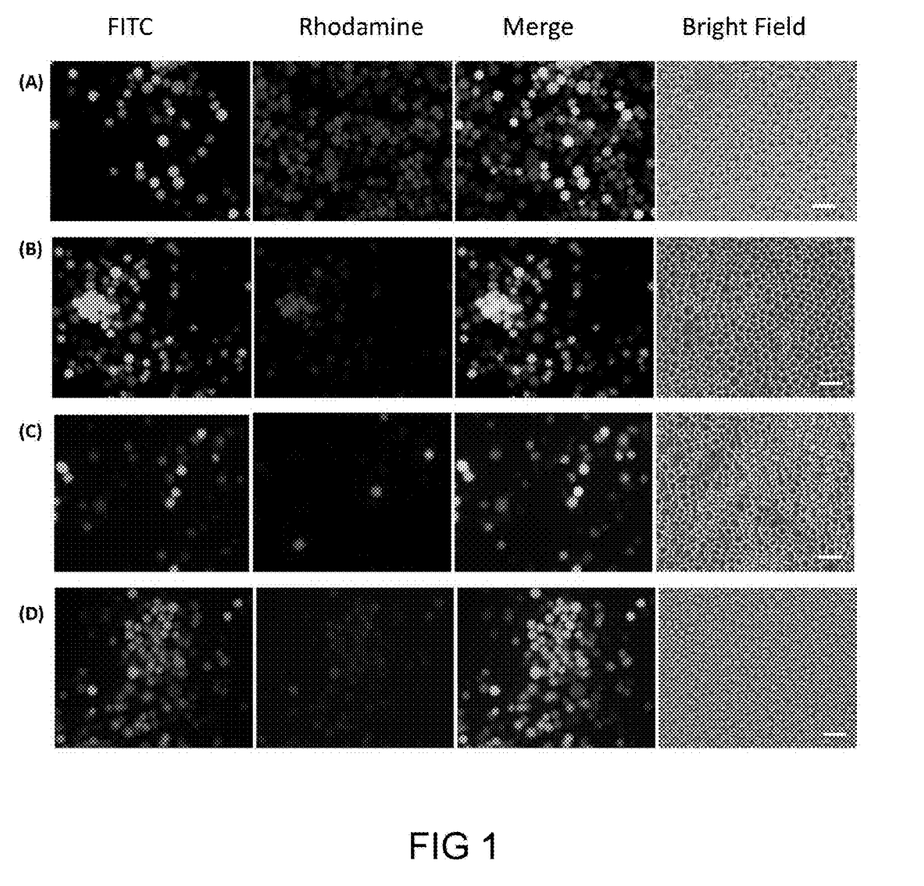
FIG. 1A are photographs of Sf21 cells co-infected with egfp-Mavi virus of example 1.1.1 and Ac-DsRed virus of example 1.1.2, the photographs were taken under FITC, rodamine and merge filters in accordance with one embodiment of the present disclosure.
FIG. 1B are photographs of Sf21 cells infected with virus derived from a single plaque, the photographs were taken under FITC, rodamine and merge filters in accordance with one embodiment of the present disclosure.
FIG. 1C are photographs of NTU-MV532 cells infected with culture medium collected from a single plaque of Sf21 cells, which were co-infected with egfp-Mavi virus of example 1.1.1 and Ac-DsRed virus of example 1.1.2, the photographs were taken under FITC, rodamine and merge filters in accordance with one embodiment of the present disclosure.
FIG. 1D are photographs of NTU-MV532 cells infected with virus derived from a single plaque, the photographs were taken under FITC, rodamine and merge filters in accordance with one embodiment of the present disclosure.

Five days post-infection, the culture medium in cells as depicted in FIG. 1B was again collected and used to infect MaviMNPV-permissive cells (i.e., NTU-MV532 cells). Since the viruses derived from the culture medium of cells in FIG. 1B were released from Sf21, they would include "wild type" viruses that cannot infect NTU-MV532 cells, as well as the target hybrid viruses that infect both the Sf21 and NTU-MV532 cells. As illustrated in FIG. 1C, two different populations of viruses, both capable of infecting NTU-MV532 cells and emitted red or green fluorescence were generated. Subsequently, the culture medium was collected and used to conduct the end point dilution in NTU-MV532 cells to isolate the single viral clones. Photographs from a single plaque in NTU-MV532 cells are illustrated in FIG. 1D. A desired hybrid AcMv virus was eventually selected from the single viral plaque.

Example 2

Characterization of the Hybrid AcMv Baculovirus of Example 1.2

The selected desired hybrid AcMv virus of Example 1.2 was subject to further analysis including cross host infection analysis and whole genome sequencing.

2.1 Cross Host Infection Analysis

Figure 2:
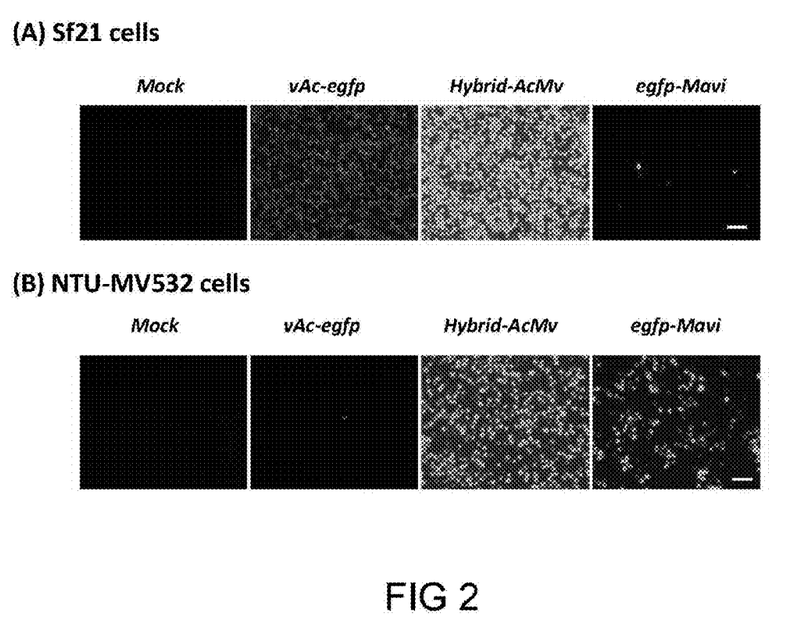
FIG. 2A are photographs of Sf21 cells respectively infected with Ac-egfp of example 1.1.3, the hybrid AcMv of example 1.2 and egfp-Mavi of example 1.1.1 in according to one embodiment of the present disclosure.
FIG. 2B are photographs of NTU-MV532 respectively infected with Ac-egfp of example 1.1.3, the hybrid AcMv of example 1.2 and egfp-Mavi of example 1.1.1 in according to one embodiment of the present disclosure.

To test whether the selected hybrid AcMv virus of Example 1.2 did possess cross host infection capability, both AcMNPV-permissive cells (e.g., Sf21 or Hi-5 cells) and MaviMNPV-permissive cells (e.g., NTU-MV532 cells) were infected with the selected hybrid AcMv virus of Example 1.2, and the infection was monitored by the measurement of green fluorescence emitted by the expressed EGFP. Results are illustrated in FIGS. 2 and 3.

For Sf21 cells, which are permissive to AcMNPV and non-permissive to MaviMNPV, hence only cells infected with AcMNPV (i.e., Ac-egfp) and/or hybrid AcMv virus were capable of emitting green fluorescence, whereas no fluorescence was observed for cells infected with MaviMNPV (i.e., egfp-Mavi) (FIG. 2A). Similar results were also observed in NTU-MV532 cells, which are permissive to MaviMNPV and non-permissive to AcMNPV. As illustrated in FIG. 2B, only cells infected with egfp-Mavi and hybrid AcMv virus were capable of emitting green fluorescence, whereas no fluorescence was observed in Ac-egfp infected cells.

Figure 3:
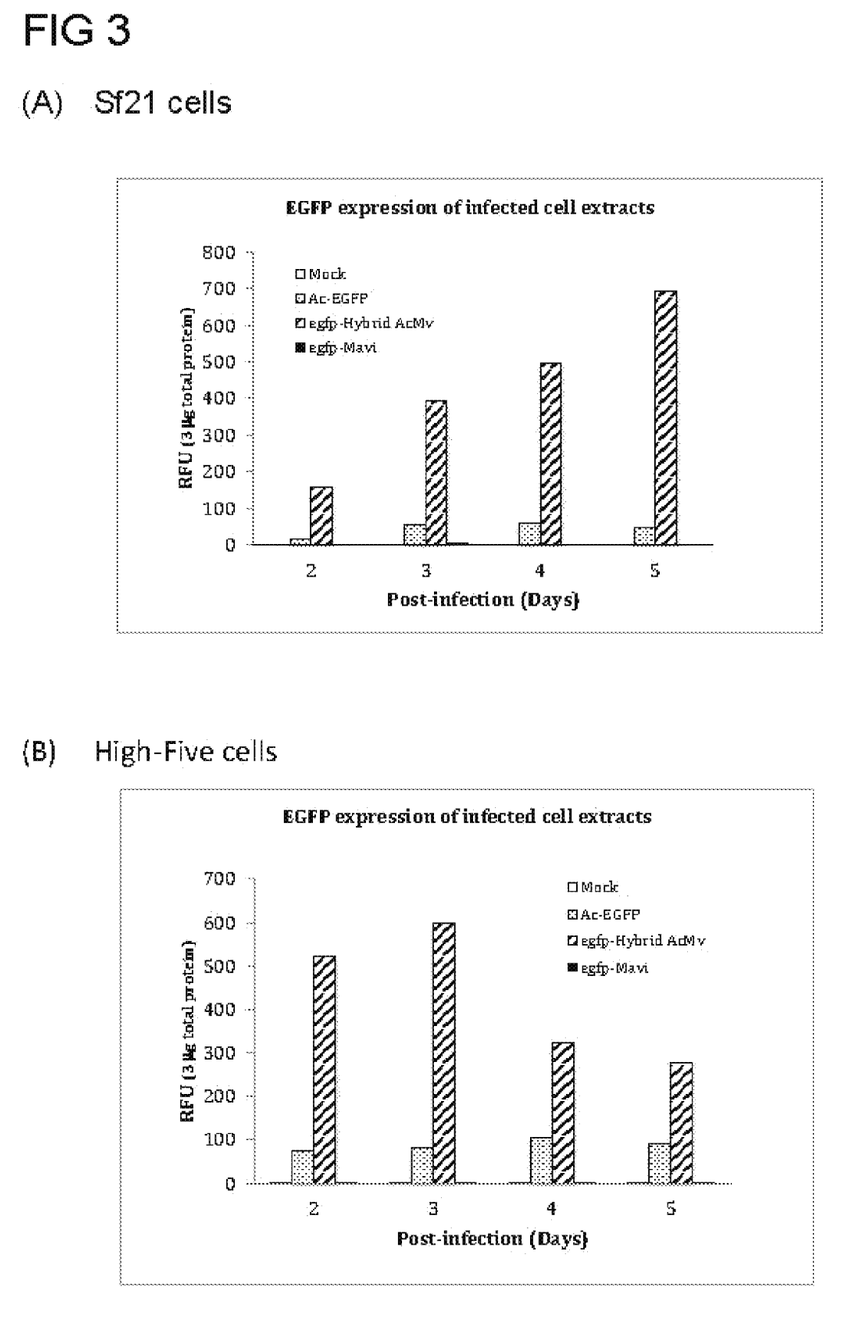
FIGS. 3A to 3B are bar diagrams illustrating quantification expression of EGFP in (A) Sf21 cells, (B) Hi-5 cells and (C) NTU-MV532 cells resulted from the infected hybrid AcMv virus of Example 1.2 in according to one embodiment of the present disclosure.
Figure 4:
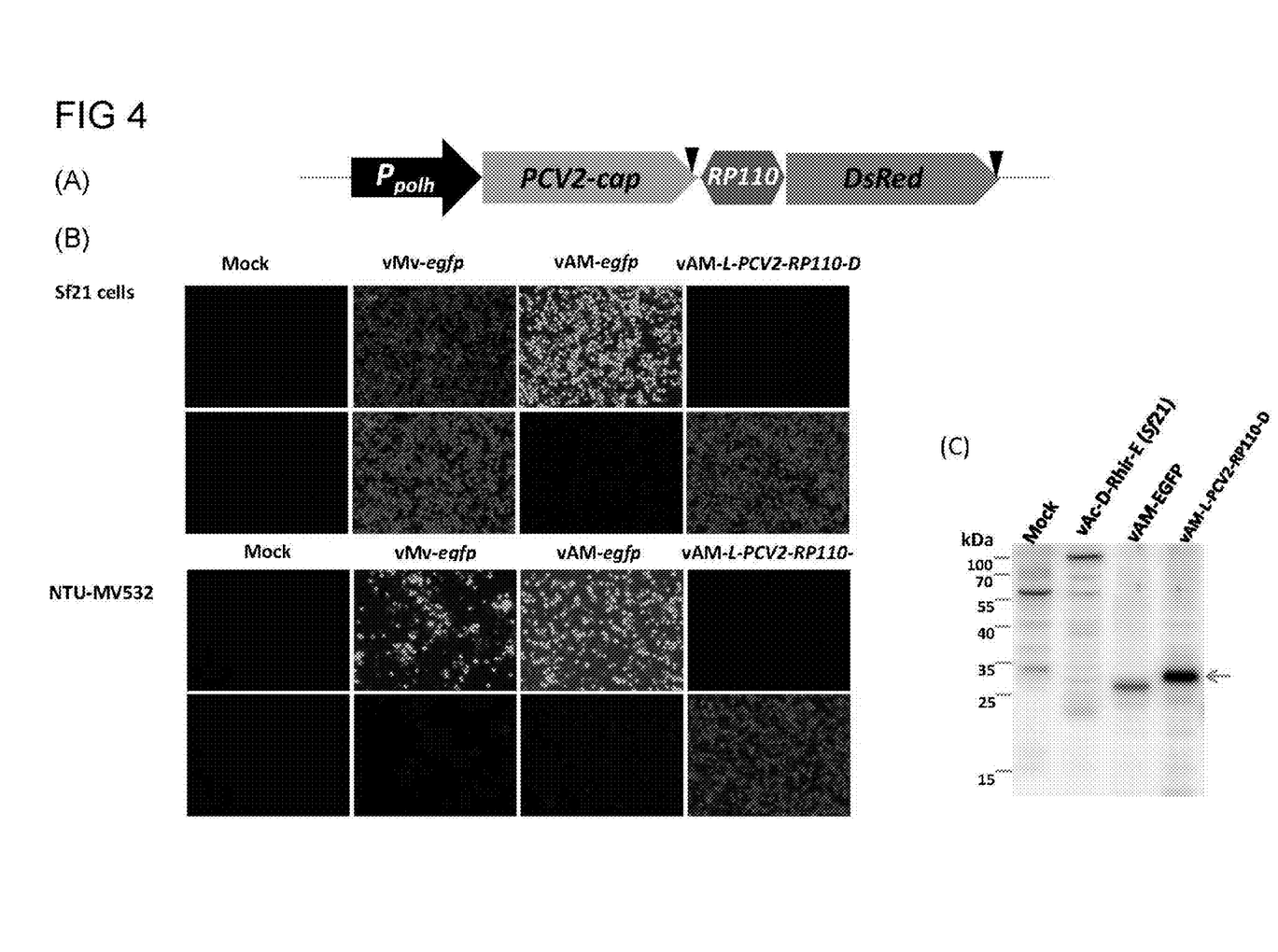
FIG. 4A is a schematic diagram of the PCV2-cap containing-transfer vector constructed in accordance with one embodiment of the present disclosure.
FIG. 4B are photographs of Sf21 cells and NTU-MV532 cells respectively infected with the recombinant virus containing PCV2-cap gene (i.e., vAM-L-PCV2-RP110-D) and the control hybrid AcMv virus of Example 1.2 (i.e., vAM-egfp) in accordance with one embodiment of the present disclosure; in which vAc-D-Rhir-E and egfp-Mavi were respectively used as positive controls to infect Sf21 cells and NTU-MV532 cells.
FIG. 4C is the western blot analysis of protein extracts derived from the NTU-MV532 cells infected with the PCV2-cap containing-recombinant virus (i.e., vAM-L-PCV2-RP110-D) or the control hybrid AcMv virus of Example 1.2 (i.e., vAM-egfp) in accordance with one embodiment of the present disclosure; in whcih protein extracts derived from the Sf21 cells infected with the control virus, (i.e., vAc-D-Rhir-E), served as a negative control.

The respective time courses of the expressed EGFP in AcMNPV-permissive and MaviMNPV-permissive cells resulted from the infected hybrid AcMv virus of Example 1.2 were also analyzed, and results are depicted in FIG. 3.

For AcMNPV-permissive cells, the level of EGFP in Sf21 cells infected with hybrid AcMv virus of Example 1.2 or Ac-egfp started to increase on the second day post infection, and reached its peak on the fifth day; whereas the expressed level of EGFP remained relatively unchanged if cells were infected with egfp-Mavi (FIG. 3A). Similar observation was also found in another AcMNPV-permissive cells, that is, Hi-5 cells (FIG. 3B). In contrast, to MaviMNPV-permissive NTU-MV532 cells, green fluorescence was observed in both egfp-Mavi infected- and hybrid AcMv virus infected cells but not those infected with Ac-egfp (FIG. 3C).

Taken together, the results in FIGS. 2 to 3 confirm that the selected hybrid AcMv virus of Example 1.2 does possess cross host infection capability.

2.2 Whole Genome Sequencing

To identify the genes responsible for the cross host infection capability of the hybrid AcMv virus of Example 1.2, the virus was subject to whole genome sequencing, and sequence identity of each gene was then compared with corresponding AcMNPV and MaviMNPV genes. The results are summarized in Table 1.

As evidenced from Table 1, the hybrid AcMv virus of Example 1.2 obviously possessed a backbone of AcMNPV, with 90% of genes identical to those of AcMNPV, and only those near the polyhedron locus of AcMNPV were replaced by approximately 10-kb DNA fragment of MaviMNPV. ORFs derived from MaviMNPV included, EGFP, ORF1629, pk1, CDS1, CDS2, lef1, pe38, CDS57, ptp, CDS58, CDS59, and lef2. In addition, some hybrid ORFs were generated as well, which included egt (SEQ ID NO: 1) and Orf152 (SEQ ID NO: 2).

TABLE 1

Comparison of homologous ORFs among hybrid AcMv virus of example 1.2, AcMNPV and/MaviMNPV

| ORF | Name* | AcMNPV | MaviMNPV |
|---|---|---|---|
| 1 | Mv-EGFP | — | Mv-EGFP (100) |
| 2 | Mv-ORF1629 | Ac9 (82.1) | Mv2 (100) |
| 3 | Mv-pk1 | Ac10 (89.8) | Mv3 (100) |
| 4 | Mv-CDS1 | Ac11 (85.4) | Mv4 (100) |
| 5 | Mv-CDS2 | Ac13 (87.1) | Mv5 (99.8) |
| 6 | Mv-lef1 | Ac14 (87.9) | Mv6 (99.7) |
| 7 | Hybrid-egt | Ac15 (86.8) | Mv7 (86.8) |
| 8 | Ac-Orf16 | Ac16 (99.9) | Mv8 (78.3) |
| 9 | Ac-Orf17 | Ac17 (100) | Mv9 (62.7) |
| 10 | Ac-Orf18 | Ac18 (100) | Mv10 (87.8) |
| 11 | Ac-Orf19 | Ac19 (100) | Mv11 (89.7) |
| 12 | Ac-Orf20 | Ac20 (99.9) | — |
| 13 | Ac-Orf21 | Ac21 (99.9) | Mv12 (59.7) |
| 14 | Ac-Orf22 | Ac22 (100) | Mv13 (90.1) |
| 15 | Ac-env-prot | Ac23 (100) | Mv14 (75.4) |
| 16 | Ac-pkip | Ac24 (100) | Mv15 (83) |
| 17 | Ac-Orf25 | Ac25 (99.9) | Mv16 (88.3) |
| 18 | Ac-Orf26 | Ac26 (100) | Mv17 (88.7) |
| 19 | Ac-IAP1 | Ac27 (100) | Mv18 (75.6) |
| 20 | Ac-lef6 | Ac28 (100) | Mv19 (47.1) |
| 21 | Ac-Orf29 | Ac29 (100) | Mv20 (56.9) |
| 22 | Ac-Orf30 | Ac30 (99.9) | Mv21 (83.7) |
| 23 | Ac-sod Hr2 | Ac31 (100) | Mv22 (85.0) |
| 24 | Ac-fgf | Ac32 (100) | — |
| 25 | Ac-HisP | Ac33 (100) | — |
| 26 | Ac-Orf34 | Ac34 (98.0) | Mv23 (82.4) |
| 27 | Ac-v-ubi | Ac35 (100) | Mv24 (91.0) |
| 28 | Ac-39K/pp31 | Ac36 (100) | Mv25 (81.7) |
| 29 | Ac-lef11 | Ac37 (100) | Mv26 (87.3) |
| 30 | Ac-Orf38 | Ac38 (100) | Mv27 (88.0) |
| 31 | Ac-p43 | Ac39 (100) | Mv28 (80.7) |
| 32 | Ac-p47 | Ac40 (99.7) | Mv29 (89.6) |
| 33 | Ac-Orf41 | Ac41 (99.3) | Mv30 (86.4) |
| 34 | Ac-GTA | Ac42 (99.5) | — |
| 35 | Ac-Orf43 | Ac43 (100) | Mv31 (82.9) |
| 36 | Ac-Orf44 | Ac44 (100) | Mv32 (87.4) |
| 37 | Ac-Orf45 | Ac45 (99.8) | Mv33 (81.1) |
| 38 | Ac-odv-e66 | Ac46 (100) | — |
| 39 | Ac-Orf47 | AC47 (100) | Mv34 (84.3) |
| 40 | Ac-Orf48 | Ac48 (100) | — |
| 41 | AC-pcna | Ac49 (100) | — |
| 42 | Ac-lef8 | Ac50 (100) | Mv35 (90.3) |
| 43 | Ac-Orf51 | Ac51 (99.9) | Mv36 (88.3) |
| 44 | Ac-Orf52 | Ac52 (99.7) | Mv37 (54) |
| 45 | Ac-Orf53 | Ac53 (99.8) | Mv38 (90.7) |
| 46 | Ac-lef10 | Ac53a (100) | Mv39 (90.3) |
| 47 | Ac-Orf54 | Ac54 (99.9) | Mv40 (89.2) |
| 48 | Ac-Orf55 | Ac55 (100) | Mv41 (80.2) |
| 49 | Ac-Orf56 | Ac56 (100) | Mv42 (89.8) |
| 50 | Ac-Orf57 | Ac57 (99.8) | — |
| 51 | Ac-Orf58 | Ac58 (99.4) | Mv43 (23.6) |
| 52 | Ac-Orf59 | Ac59 (99.5) | Mv43 (39.7) |
| 53 | Ac-Orf60 | Ac60 (100) | Mv44 (86.4) |
| 54 | Ac-FP Hr2a | Ac61 (100) | Mv45 (88.2) |
| 55 | Ac-lef9 | Ac62 (99.9) | Mv46 (95.6) |
| 56 | AC-Orf63 | AC63 (99.8) | Mv47 (83.8) |
| 57 | Ac-gp37 | Ac64 (100) | Mv48 (85.0) |
| 58 | Ac-DNA-pol | Ac65 (100) | Mv49 (89.7) |
| 59 | Ac-Orf66 | Ac66 (100) | Mv50 (82.3) |
| 60 | Ac-lef3 | Ac67 (99.9) | Mv51 (83.3) |
| 61 | Ac-Orf68 | Ac68 (100) | Mv52 (85.7) |
| 62 | Ac-Orf69 | Ac69 (100) | Mv53 (86.9) |
| 63 | Ac-Orf70 | Ac70 (99.4) | Mv54 (86.5) |
| 64 | Ac-IAP2 | Ac71 (100) | Mv54 (80.5) |
| 65 | Ac-Orf72 | Ac72 (100) | Mv55 (84.2) |
| 66 | Ac-Orf73 | Ac73 (99.7) | Mv56 (86.0) |
| 67 | Ac-Orf74 | Ac74 (99.9) | Mv57 (84.2) |
| 68 | Ac-Orf75 | Ac75 (100) | Mv58 (89.3) |
| 69 | Ac-Orf76 | Ac76 (100) | Mv59 (87.8) |
| 70 | Ac-vlf-1 | Ac77 (99.9) | Mv60 (90.9) |
| 71 | Ac-Orf78 | Ac78 (100) | Mv61 (87.4) |
| 72 | Ac-Orf79 | Ac79 (99.7) | Mv62 (91.7) |
| 73 | Ac-gp41 | Ac80 (100) | Mv63 (90.7) |
| 74 | Ac-Orf81 | Ac81 (99.9) | Mv64 (87.8) |
| 75 | Ac-TLP | Ac82 (99.8) | Mv65 (86.6) |
| 76 | Ac-p95 Hr3 | Ac83 (99.9) | Mv66 (86.0) |
| 77 | Ac-Orf84 | Ac84 (99.6) | — |
| 78 | Ac-Orf85 | Ac85 (100) | — |
| 79 | Ac-PNK/PNL | Ac86 (100) | — |
| 80 | Ac-p15 | Ac87 (99.7) | — |
| 81 | Ac-cg30 | Ac88 (100) | — |
| 82 | Ac-vp39 | Ac89 (100) | Mv67 (87.7) |
| 83 | Ac-lef4 | Ac90 (100) | Mv68 (88.9) |
| 84 | Ac-Orf91 | Ac91 (99.6) | — |
| 85 | Ac-Orf92 | Ac92 (100) | Mv69 (90.8) |
| 86 | Ac-Orf93 | Ac93 (100) | Mv70 (90.0) |
| 87 | Ac-odv-e25 | Ac94 (99.4) | Mv71 (86.2) |
| 88 | Ac-helicase | Ac95 (99.6) | Mv72 (89.0) |
| 89 | Ac-Orf96 | Ac96 (100) | Mv73 (86.3) |
| 90 | Ac-Orf97 | Ac97 (100) | — |
| 91 | Ac-38K | Ac98 (100) | Mv75 (86.7) |
| 92 | Ac-lef5 | Ac99 (99.7) | Mv76 (92.0) |
| 93 | Ac-p6.9 | Ac100 (100) | Mv77 (90.5) |
| 94 | Ac-p40 | Ac101 (100) | Mv78 (89.3) |
| 95 | Ac-Orf102 | Ac102 (100) | Mv79 (81.5) |
| 96 | Ac-p48 | Ac103 (100) | Mv80 (90.8) |
| 97 | Ac-vp80 | Ac104 (99.9) | Mv81 (88.4) |
| 98 | Ac-HE65 Hr4a | Ac105 (100) | Mv82 (42.6) |
| 99 | Ac-Orf106 | Ac106 (96.9) | Mv83 (24.4) |
| 100 | Ac-Orf107 | Ac107 (97.6) | Mv83 (39.5) |
| 101 | Ac-Orf108 | Ac108 (99.7) | Mv84 (88.4) |
| 102 | Ac-Orf109 | Ac109 (99.7) | Mv85 (89.5) |
| 103 | Ac-Orf110 | Ac110 (98.8) | Mv86 (92.4) |
| 104 | Ac-Orf111 | Ac111 (100) | Mv87 (75.8) |
| 105 | Ac-Orf112 | Ac112 (99.2) | — |
| 106 | Ac-Orf113 Hr4b | Ac113 (99.6) | — |
| 107 | Ac-Orf114 | Ac114 (99.8) | Mv88 (85.4) |
| 108 | Ac-Orf115 | Ac115 (99.8) | Mv89 (89.9) |
| 109 | Ac-Orf116 | Ac116 (100) | — |
| 110 | Ac-Orf117 | Ac117 (100) | Mv90 (84.4) |
| 111 | Ac-Orf118 | Ac118 (100) | — |
| 112 | Ac-Orf119 | Ac119 (99.7) | Mv91 (86.5) |
| 113 | Ac-Orf120 Hr4c | Ac120 (99.2) | Mv92 (84.3) |
| 114 | Ac-Orf121 | Ac121 (100) | — |
| 115 | Ac-Orf122 | Ac122 (99.5) | — |
| 116 | Ac-pk2 | AC123 (99.7) | — |
| 117 | Ac-Orf124 | Ac124 (99.9) | Mv93 (84.8) |
| 118 | Ac-lef7 | Ac125 (100) | Mv94 (73.4) |
| 119 | Ac-chitinase | Ac126 (98.6) | Mv95 (88.2) |
| 120 | Ac-v-cath | Ac127 (99.5) | Mv96 (88.6) |
| 121 | Ac-gp64 | Ac128 (100) | Mv97 (88.3) |
| 122 | Ac-p24 | Ac129 (99.8) | Mv98 (83.9) |
| 123 | Ac-gp16 | Ac130 (100) | Mv99 (83.2) |
| 124 | Ac-PE/pp34 | Ac131 (99.7) | Mv100 (64.7) |
| 125 | Ac-Orf132 | Ac132 (100) | Mv101 (84.7) |
| 126 | Ac-alk-exo | Ac133 (99.9) | Mv102 (90.0) |
| 127 | Ac-94K | Ac134 (99.9) | — |
| 128 | Ac-35K/p35 Hr5 | Ac135 (100) | Mv103 (84.9) |
| 129 | Ac-p26 | Ac136 (100) | Mv104 (84.2) |
| 130 | Ac-p10 | Ac137 (99.6) | Mv105 (61.1) |
| 131 | Ac-p74 | Ac138 (99.8) | Mv106 (87.6) |
| 132 | Ac-ME53 | Ac139 (99.8) | Mv107 (76.9) |

TABLE 1-continued

Comparison of homologous ORFs among hybrid AcMv virus of example 1.2, AcMNPV and/MaviMNPV

| | | Homologues (% identity) | |
|---|---|---|---|
| ORF | Name* | AcMNPV | MaviMNPV |
| 133 | Ac-Orf140 | Ac140 (100) | Mv108 (31.9) |
| 134 | Ac-IE-O | Ac141 (100) | Mv109 (88.8) |
| 135 | Ac-49K | Ac142 (99.8) | Mv110 (90.4) |
| 136 | Ac-odv-e18 | Ac143 (100) | Mv111 (55.3) |
| 137 | Ac-odv-e27 | Ac144 (100) | Mv112 (91.8) |
| 138 | Ac-IE-01 | Ac141a (99.9) | — |
| 139 | Ac-Orf145 | Ac145 (100) | Mv113 (70.1) |
| 140 | Ac-Orf146 | Ac146 (100) | Mv114 (76.8) |
| 141 | Ac-IE-1 | Ac147 (99.9) | Mv115 (86.6) |
| 142 | AC-odv-e56 | Ac148 (100) | Mv116 (84.7) |
| 143 | Ac-Orf149 | Ac149 (100) | Mv117 (49.7) |
| 144 | Ac-Orf150 | Ac150 (100) | Mv118 (43.1) |
| 145 | Ac-IE-2 | Ac151 (99.9) | Mv119 (64.2) |
| 146 | Hybdrid-Orf152 | Ac152 (94.6) | Mv120 (61.8) |
| 147 | Mv-pe38 | Ac153 (62.9) | Mv121 (100) |
| 148 | Mv-CDS57 | Ac154 (71.5) | Mv122 (100) |
| Hr1 | | | |
| 149 | Mv-ptp | Ac1 (78.7) | Mv123 (100) |
| 150 | Mv-CDS58 | Ac4 (25.4) | Mv124 (100) |
| 151 | Mv-CDS59 | Ac5 (75.7) | Mv125 (100) |
| 152 | Mv-lef2 | Ac6 (84.2) | Mv126 (100) |

Example 3

Production of Exogenous Protein by Hybrid AcMv Baculovirus of Example 1.2

In this example, to verify whether the hybrid AcMv baculovirus of example 1.2 may help producing proteins in two different host cells, (i.e., AcMNPV-permissive cells and MaviMNPV-permissive cells), PCV2-cap was used as an example of an exogenous protein, and a transfer vector containing PCV2-cap was constructed in according to procedures described in example 1.1.4 (i.e., pMv-L-PCV2-RP110-DsRed). FIG. 4A is a schematic diagram of the transfer vector containing PCV2-cap of example 1.1.4. The transfer vector was then used with the hybrid AcMv baculovirus of example 1.2 to co-transfect both types of host cells, (i.e., Sf21 cells, and NTU-MV532 cells), and a single hybrid virus strain containing the PCV2-cap gene was eventually selected. The selected hybrid virus strain was then used to infect the host cell (i.e., Sf21 cells and NTU-MV532 cells) and the infected host cells were subsequently cultivated at 27° C. for 3-4 days to allow the expression of PCV2-cap. As a positive control, vAc-D-Rhir-E and egfp-Mavi were used to infect Sf21 cells and NTU-MV532 cells, respectively. Results are depicted in FIG. 4B and FIG. 4C.

In Sf21 cells, since they are permissive to AcMNPV, hence cells infected with the control hybrid AcMv virus of Example 1.2 (i.e., vAM-egfp) were capable of expressing EGFP and thus produced green fluorescence (FIG. 4B, Sf21 cells, upper panel), whereas cells infected with the recombinant virus containing PCV2-cap gene (i.e., vAM-L-PCV2-RP110-D) would express both PCV2-cap and DsRed, and therefore red fluorescence was produced (FIG. 4B, Sf21 cells, lower panel).

Similar observation was also found in NTU-MV532 cells, in which green fluorescence was produced in cells infected with the control hybrid AcMv virus of Example 1.2 (i.e., vAM-egfp) (FIG. 4B, NTU-MV532 cells, upper panel); whereas red fluorescence was observed in cells infected with the recombinant virus containing PCV2-cap gene (i.e., vAM-L-PCV2-RP110-D) (FIG. 4B, NTU-MV532 cells, lower panel).

PCV2-cap harvested from the infected host cells were also analyzed by coomassie blue staining (data not shown) and further confirmed by western blot analysis. In western blot analysis, the anti-PCV2 antibody was used to detect PCV2-cap protein (FIG. 4C).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An *Autographa californica* multiple nucleopolyhedrovirus (AcMNPV) based hybrid baculovirus capable of infecting different hosts comprising Maruca vitrata multiple nucleopolyhedrovirus (MaviMNPV) genes of lef1, orf1629, pk1, CDS1, CDS2, and lef2; and AcMNPV/MaviMNPV-hybrid genes of egt, wherein egt comprises the sequence of SEQ ID NO:1, and orf152, wherein orf152 comprises the sequence of SEQ ID NO:2.

2. The AcMNPV based hybrid baculovirus of claim 1, further comprising a first nucleic acid encoding a first fluorescent protein.

3. The AcMNPV based hybrid baculovirus of claim 2, wherein the first fluorescent protein is any of green fluorescence protein (GFP), enhanced green fluorescence protein (EGFP), *Discosoma* sp. red fluorescent protein (DsRed), blue fluorescence protein (BFP), enhanced yellow fluorescent proteins (EYFP), *Anemonia majano* fluorescent protein (amFP), *Zoanthus* fluorescent protein (zFP), *Discosoma* fluorescent protein (dsFP), or *Clavularia* fluorescent protein (cFP).

4. The AcMNPV based hybrid baculovirus of claim 1, wherein the hosts are AcMNPV-permissive cells or AcMNPV-permissive insect larvae.

5. The AcMNPV based hybrid baculovirus of claim 4, wherein the AcMNPV-permissive cells are any of Sf9, Sf21 or Hi-5 cells; and the AcMNPV-permissive insect larvae are *Trichoplusia ni* or *Spodoptera frugiperda*.

6. The AcMNPV based hybrid baculovirus of claim 4, wherein the hosts are MaviMNPV-permissive cells or MaviMNPV-permissive insect larvae.

7. The AcMNPV based hybrid baculovirus of claim 6, wherein the MaviMNPV-permissive cells are NTU-MV532 cells; and the MaviMNPV-permissive insect larvae are *Maruca Vitrata*.

8. A method of producing an exogenous protein in an insect host comprising:
(a) co-infecting the insect host with the AcMNPV based hybrid baculovirus of claim 2, and a transfer vector, which comprises in sequence,
a promoter;
a second nucleic acid operably linked to the promoter, wherein the second nucleic acid encodes the exogenous protein;
an IRES element; and
a third nucleic acid operably linked to the IRES element, wherein the third nucleic acid encodes a second fluorescent protein,
wherein the first and second fluorescent proteins respectively emit a first and second fluorescence, in which the first and second fluorescence are respectively emitted at different wavelengths;
(b) isolating a recombinant virus generated from the co-infected first insect host of step (a) that emits the second fluorescence;
(c) infecting a second insect host with the isolated recombinant virus of step (b); and
(d) harvesting the exogenous protein from the infected second insect host of step (c).

9. The method of claim 8, wherein the IRES element of the transfer vector is a portion of a *Rhopalosiphum padi* virus (RhPV) IRES sequence at least 90% identical to SEQ ID NO: 3.

10. The method of claim 8, wherein the hosts are AcMNPV-permissive cells or AcMNPV-permissive insect larvae.

11. The method of claim 10, wherein the AcMNPV-permissive cells are any of Sf9, Sf21 or Hi-5 cells; and the AcMNPV-permissive insect larvae are *Trichoplusia ni* or *Spodoptera frugiperda*.

12. The method of claim 8, wherein the hosts are MaviMNPV-permissive cells or MaviMNPV-permissive insect larvae.

13. The method of claim 12, wherein the MaviMNPV-permissive cells are NTU-MV532 cells; and the MaviMNPV-permissive insect larvae are *Maruca Vitrata*.

14. The method of claim 8, wherein the first and second fluorescent proteins are respectively selected from the group consisting of GFP, EGFP, DsRed, BFP, EYFP, amFP, zFP, dsFP, and cFP.

15. The method of claim 8, wherein the exogenous protein is any of an insect toxic protein, a therapeutic protein or a reporter protein.

* * * * *